United States Patent [19]

Uekita et al.

[11] Patent Number: 5,049,455
[45] Date of Patent: Sep. 17, 1991

[54] AMPHIPHILIC ANTHRACENE DERIVATIVE

[75] Inventors: Masakazu Uekita, Kobe; Yasunori Yoshioka, Ashiya, both of Japan

[73] Assignee: Kanegafuchi Kagaku Kogyo Kabushiki Kaisha, Osaka, Japan

[21] Appl. No.: 581,162

[22] Filed: Sep. 5, 1990

Related U.S. Application Data

[60] Division of Ser. No. 283,056, Dec. 7, 1988, abandoned, which is a continuation of Ser. No. 772,092, Sep. 3, 1985, abandoned.

[30] Foreign Application Priority Data

Sep. 3, 1984 [JP] Japan .................................. 59-183958

[51] Int. Cl.$^5$ ...................... B27N 9/00; C07C 53/134
[52] U.S. Cl. ..................................... 428/917; 562/496
[58] Field of Search ......................... 428/917; 562/496

[56] References Cited

PUBLICATIONS

G. G. Roberts and M. McGinnity, "Solid State Communications", vol. 32, pp. 683-686 (1979).
Takagi, M. et al., J.C.S. Perkin I, 2948-53, 1979.
Pirkle et al., J. Org. Chem. 1981, 46, 2935-2938.
Pirkle, W. H. et al., J. Org. Chem. 1980, 45, 1379-82.
CA 93 (26):246115b, Vincett et al., Thin Solid Films 71(2) 305-26, 1980.

Primary Examiner—Paul J. Killos
Attorney, Agent, or Firm—Armstrong, Nikaido, Marmelstein, Kubovcik & Murray

[57] ABSTRACT

Amphiphilic anthracene derivatives having a hydrophobic substituent and a hydrophilic substituent at 9 position and 10 position of the anthracene nucleus, respectively are disclosed. The amphiphilic anthracene derivatives have an excellent film forming property, heat resistance and electroluminescene effect.

2 Claims, 6 Drawing Sheets

AMPHIPHILIC ANTHRACENE DERIVATIVE

This application is a division of application Ser. No. 283,056 filed Dec. 7, 1988 now abandoned. which application is a continuation of application Ser. No. 772,092 filed Sept. 3, 1985 now abandoned.

BACKGROUND OF THE INVENTION

The present invention relates to an amphiphilic anthracene derivative, particularly to an amphiphilic compound which contains anthracene nucleus having a hydrophobic substituent at 9 position and a hydrophilic substituent at 10 position.

Recently, as a result of the synthesis of amphiphilic compounds capable of forming Langmuir-Blodgett films or bimolecular films, researches on amphiphilic compounds having a film forming property have been accelerated in applied technical fields as well as in scientific studies.

Amphiphilic compounds of anthracene derivatives having substituents at 9 and 10 positions represented by the formula (II):

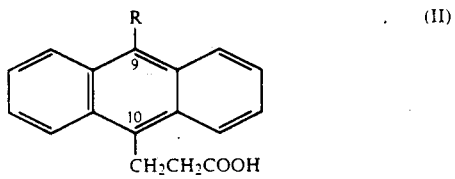

wherein R is an alkyl group of $C_4$ to $C_{12}$, have been researched by G. G. Roberts et. al., "Solid State Communications" Vol. 32, 683(1979). They reported the fact that among the amphiphilic anthracene compounds of the formula (II), the compound having a short alkyl group R, i.e. n-$C_4H_9$ can be endowed with electroluminescence effect.

When the alkyl substituent R is longer, the electroluminescence effect is reduced because the long alkyl chain acts as a barrier. Further heat resistance is lowered. On the other hand, when the alkyl substituent R is shorter, a hydrophobic property of the anthracene derivative (II) is reduced and the amphiphilic property is unbalanced, and thus it is difficult to prepare Langmuir-Blodgett films.

An object of the present invention is to provide anthracene derivatives having an improved heat resistance.

Another object of the invention is to provide amphilic anthracene derivatives which can easily form Langmuir-Blodgett films or bimolecular films being usable as an element for a photo device and an electronic device which contains insulating layers, or the like.

These and other object of the invention will become apparent from the description hereinafter.

SUMMARY OF THE INVENTION

In accordance with present invention, there is provided an amphiphilic compound of the formula (I):

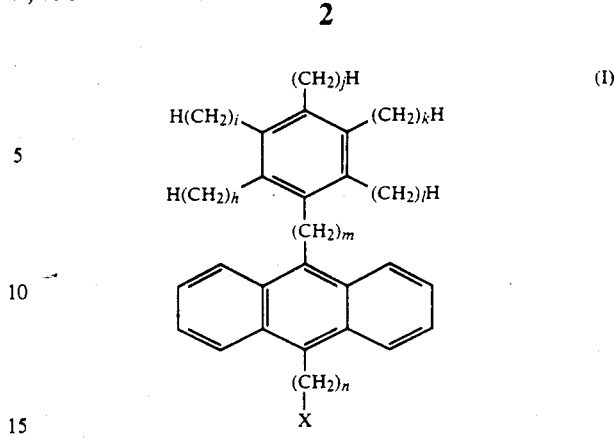

wherein X is a hydrophilic group; h, i, j, k, l, m and n are 0 or a positive integer, provided that $h+i+j+k+l+m+n \leq 10$.

DETAILED DESCRIPTION OF THE INVENTION

Figure 1:
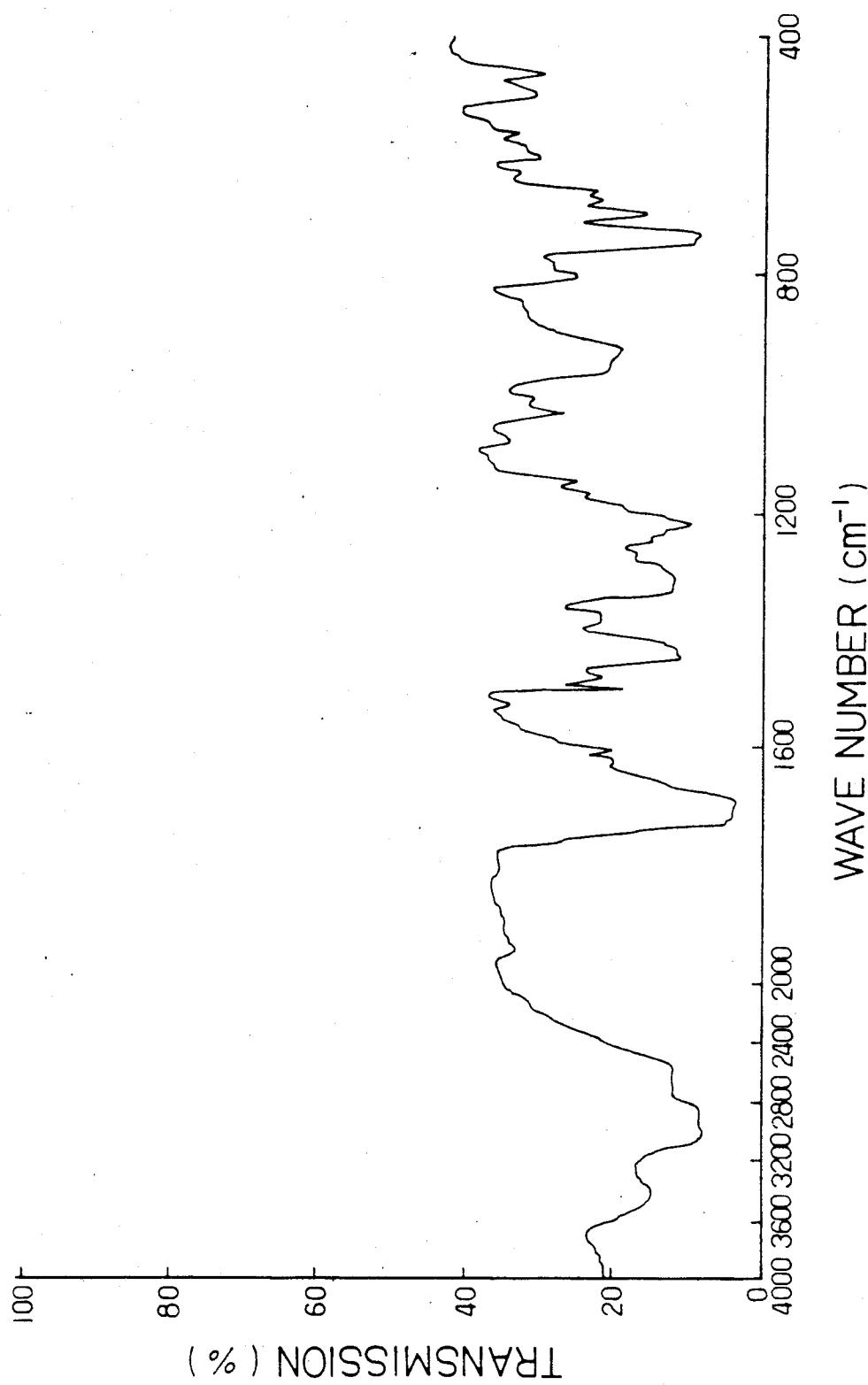
FIG. 1 is an IR spectrum chart of the free hydrolyzed product synthesized in Example 1.

The amphiphilic compound (I) of the present invention has an anthracene nucleus with a hydrophobic substituent at 9 position and a hydrophilic substituent at 10 position.

In the formula (I), the sum of h, i, j, k, l, m and n is equal to or smaller than 10, preferably equal to or smaller than 5. When the sum is larger than 10, heat resistance of the compound (I) becomes low and electroluminescence of the compound (I) is reduced due to the influence of the alkyl or alkylene groups at 9 position and 10 position, in case of utilizing its electroluminescence effect. Therefore it is desirable that the alkyl and alkylene groups bonded at 9 position and 10 position of the anthracene nucleus are as small as possible. In view of amphiphilic property, e.g. Langmuir-Blodgett film forming property, however, it is necessary that the alkyl and alkylene groups at 9 position and 10 position are bigger or longer. Considering the above-mentioned factors, it is desirable that n is 1, and more desirable that h, i, j, k and Z are 0, 1, 2 and m is 1 or 2, when n is 1. Among h, i, j, k and l, four of them are preferably 0.

As mentioned above, the hydrophobic substituent at 9 position has a phenyl group. The phenyl group may have one or more alkyl groups. Also, the phenyl group may be bonded via the methylene group —$(CH_2)_m$ to the anthracene nucleus. When m is 1 or more, two independent delocalized electron systems are separated via the methylene group. In case of this structure, the compound (I) is more stable in oxidation than in case that the phenyl group is directly bonded to the anthracene nucleus, i.e. m=0.

The hydrophilic substituent at 10 position of the anthracene nucleus is represented by the formula:

$-(CH_2)_n-X$. Nonrestrictive examples of the hydrophilic group X are, for instance, $-CH(COOR^1)_2$, $-CH(COOH)_2$, $-CH(CH_2OH)_2$, $-CH(CH_2OR^1)_2$, $-CH_2COOH$, $-CH_2COOR^1$, $-CH_2CH_2OH$, $-CH_2CH_2OR^1$, $-COOH$, $-OH$, $-NH_2$, $-CN$, $-COOR^1$, $-CONH_2$, $-SO_3H$, and the like, wherein $R^1$ is an alkyl group of $C_1$ to $C_5$. When forming Langmuir-Blodgett films, in views of the film stability on the surface of water and the stability of the built-up film on a substrate, the hydrophilic group X is preferably $-CH(COOR^1)_2$, $-CH(COOH)_2$, $-CH(CH_2OH)_2$, $-CH(CH_2OR^1)$, $-CH_2COOH$, $-CH_2COOR^1$, $CH_2CH_2OH$ or $-CH_2CH_2OR^1$, more preferably $-CH_2COOH$ or $-CH_2CH_2OH$.

The amphiphilic compound of the present invention can be prepared according to the following process, which is nonrestrictive.

Anthrone is reacted with, for example, an (alkyl-substituted phenyl)alkyl bromide of the formula:

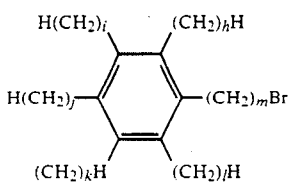

according to Grignard reaction to prepare a 9-[(alkyl-substituted phenyl)alkyl]anthracene.

The reaction conditions vary on kinds of (alkyl-substituted phenyl)alkyl bromides. Typically 1 mole of anthrone in warm benzene is added dropwise to about 1 to 4 moles of a Grignard reagent prepared by using an (alkyl-substituted phenyl)alkyl bromide in dry ethyl ether or tetrahydrofuran, and reacted at about 20° to 35° C. for 0.5 to 2 hours. After separating an organic layer, the organic layer is subjected to purification by means of column chromatography with an active alumina or by means of recrystallization to give a 9-[(alkyl-substituted phenyl)alkyl]anthracene in an yield of about 30 to 70 %.

Chloromethyl substituent is introduced at 10 position of the resulting 9-[(alkyl-substituted phenyl)alkyl]anthracene by means of a usual chloromethylation (yield: about 50 to 80 %).

0.8 To 1.2 moles of the 9-(alkyl-substituted phenyl)alkyl-1-chloromethylanthracene, preferably dissolved in benzene is added to a cooled solution of $NaCH(COOC_2H_5)$ which is separately prepared by reacting, for example, 1.5 moles of ethyl malonate and 1.25 gram atoms of metallic sodium in a solvent such as benzene. The reaction is carried out at ordinary temperature for about 10 hours, and then at a refluxing temperature for about 4 to about 6 hours to obtain a malonate reaction product represented by the formula (III) illustrated in the scheme described hereinafter (yield: about 70 to 80%.

In case of reducing the malonate reaction product (III) with $LiAlH_4$, a diol compound represented by the formula (IIIa). Alternatively, the malonate reaction product (III) is hydrolyzed with an alkali, and then acidified to obtain a dicarboxylic acid compound represented by the formula (IIIb). The dicarboxylic acid compound (IIIb) is thermally decomposed to obtain a 8-[9-(alkyl-substituted phenyl)alkyl-10-anthryl]propionic acid (IV).

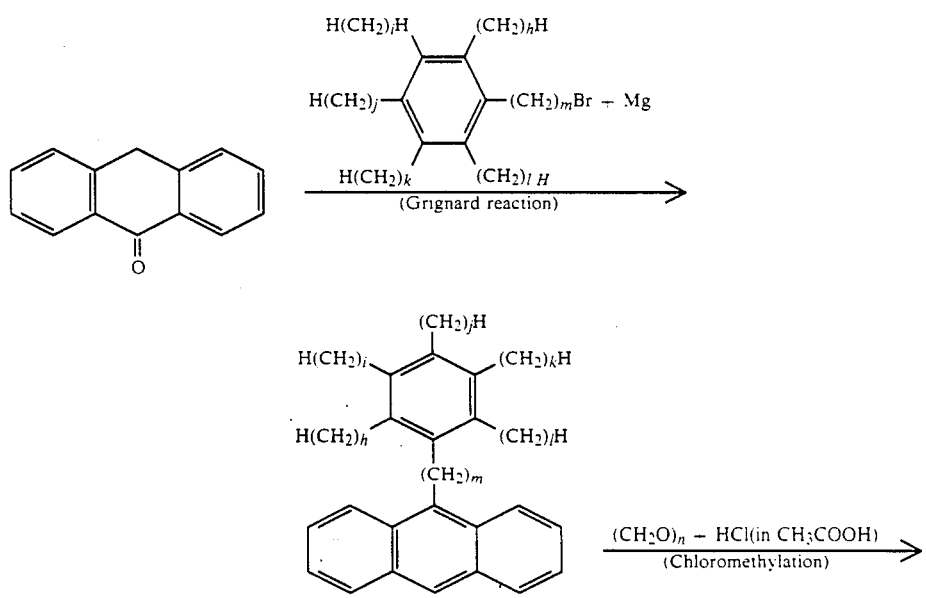

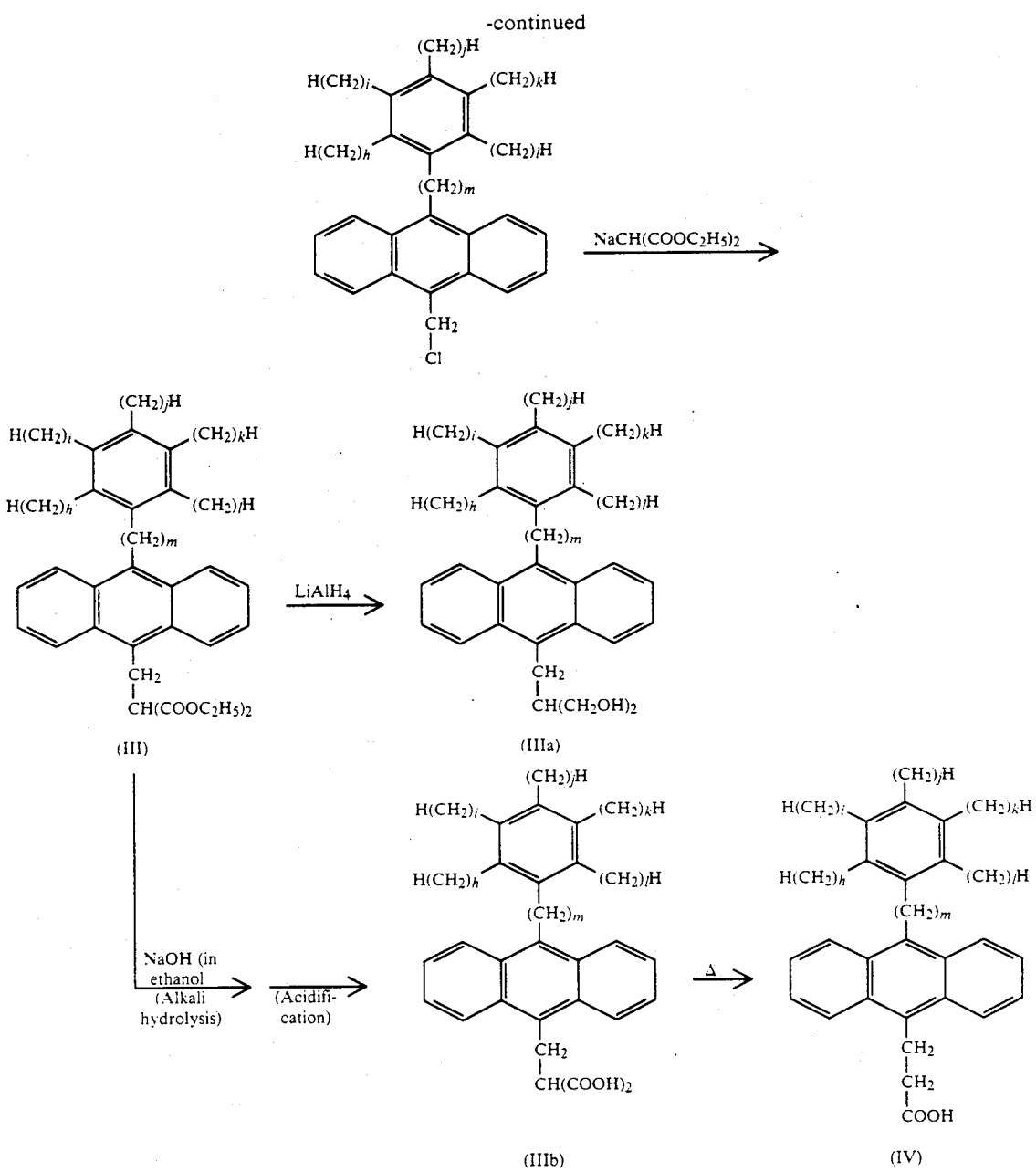

The amphiphilic compound (I) of the present invention can be utilized in various fields, particularly is usable as a film forming material for Langmuir-Blodgett films or bimolecular films. The obtained films have a high heat resistance due to a high melting point of the compound (I), and have an excellent electrically insulating property and electroluminescence property. The electroluminescence effect of the compound (I) is about 10 times larger than that of the compound where the hydrophobic substituent is n-C$_4$H$_9$.

The film can be utilized as an element of various devices having an MIS (metal/insulator/semiconductor) structure, an MIM (metal/insulator/metal) structure or the like, such as an electroluminescence device, a fluorescent device for sensing radioactive rays, a hot electron device and a photosensor.

The present invention is more specifically described and explained by means of the following Examples, and it is to be understood that the present invention is not limited to the Examples.

EXAMPLE 1

According to a method reported by Sieglitz and Marx, Berichte 56, 1619(1923) and by F. H. C. Stuart, Australian J. Chem., 478(1960), 8.2 g of 9-benzyl-anthracene was synthesized from 18.9 g of anthrone and 50 g of benzyl bromide. A solution of 4.8 g of 9-benzyl bromide in 40 ml of acetic acid was chloromethylated with 3.2 g of paraformaldehyde and hydrochloride gas to give 3.4 g of 9-benzyl-10-chloromethylanthracene (mp: 146° to 147° C.) after recrystallization from benzene.

Separately, a solution was prepared by heating a mixture of 2.07 g of diethyl malonate, 20 ml of dry benzene and 0.284 g of a chopped metallic sodium at 80° C. for 5 hours, and then cooling. To the cooled solution, a solution of 3.16 g of 9-benzyl-10-chloromethylanthracene in 50 ml of dry benzene was added dropwise. After allowing to stand over one night, the mixture was refluxed for 4 hours, and cooled, and then 80 ml of water was added thereto. The benzene-soluble layer was dried and evaporated to give 5.4 g of a crude malonate reaction product.

The crude malonate product was hydrolyzed by refluxing with 4 g of sodium hydroxide and 80 ml of ethanol for 30 minutes, and then cooled to precipitate a sodium salt of the hydrolyzed product. After the sodium salt was collected and dissolved in water, a free hydrolyzed product was precipitated by acidifying the aqueous solution with hydrochloride, and collected by means of filtration, washed with ethanol, and then dried (yield: 2.8 g; mp: 190° to 191° C.). The IR spectrum chart (KBr) is shown in FIG. 1.

The free hydrolyzed product was heated in an oil bath of 210° to 220° C. for 15 minutes, and then cooled to obtain a solid product. After recrystallizing the solid product from benzene, 1.5 g of a pale yellow needle-like crystal (mp: 196° to 197° C.) was obtained. As a result of the following analyses, the crystal was identified as β-(9-benzyl-10-anthryl)propionic acid.

Figure 2:
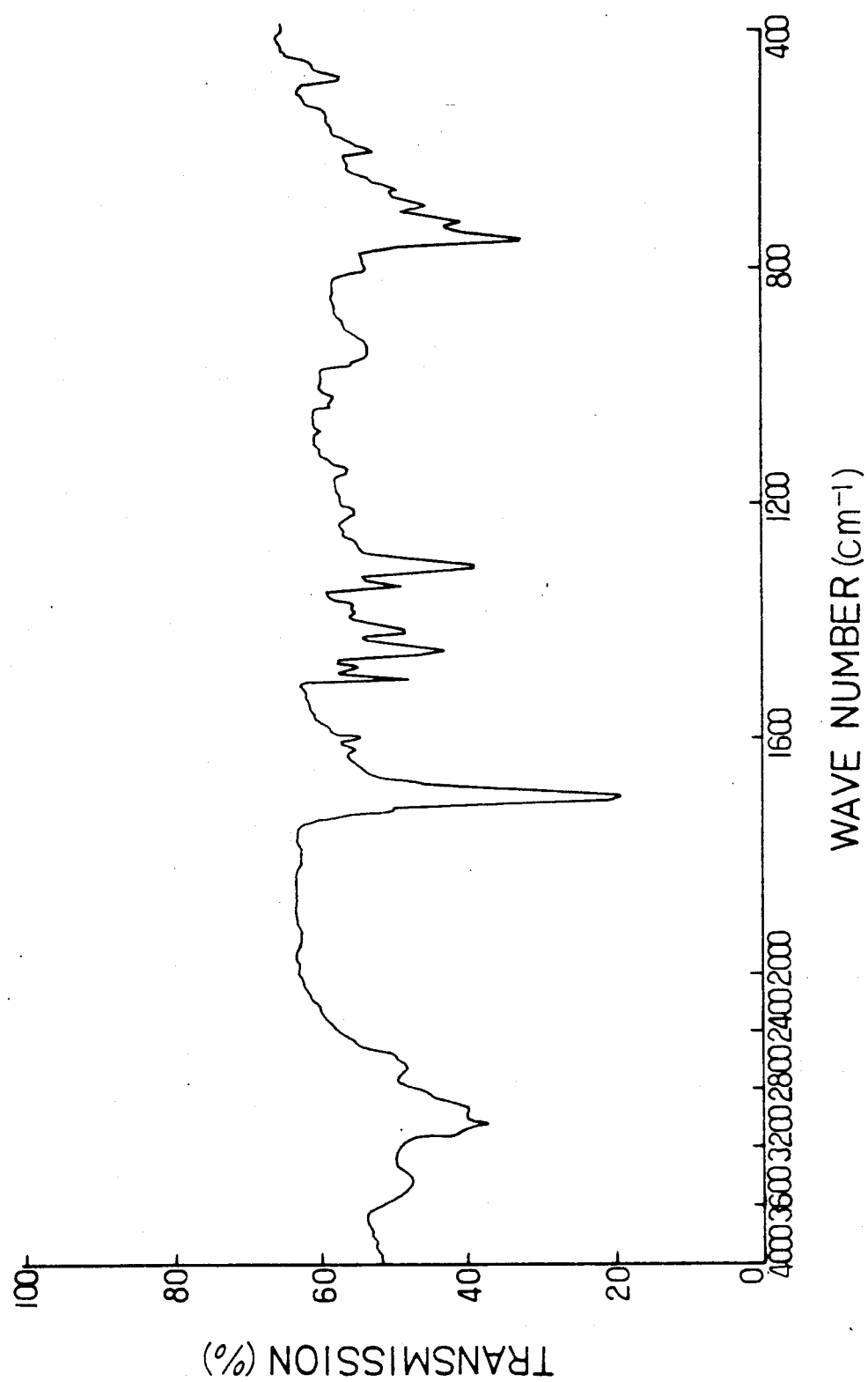
FIGS. 2 and 3 are an IR spectrum chart and an NMR spectrum chart of β-(9-benzyl-10-anthryl)propionic acid synthesized in Example 1, respectively.
Figure 3:
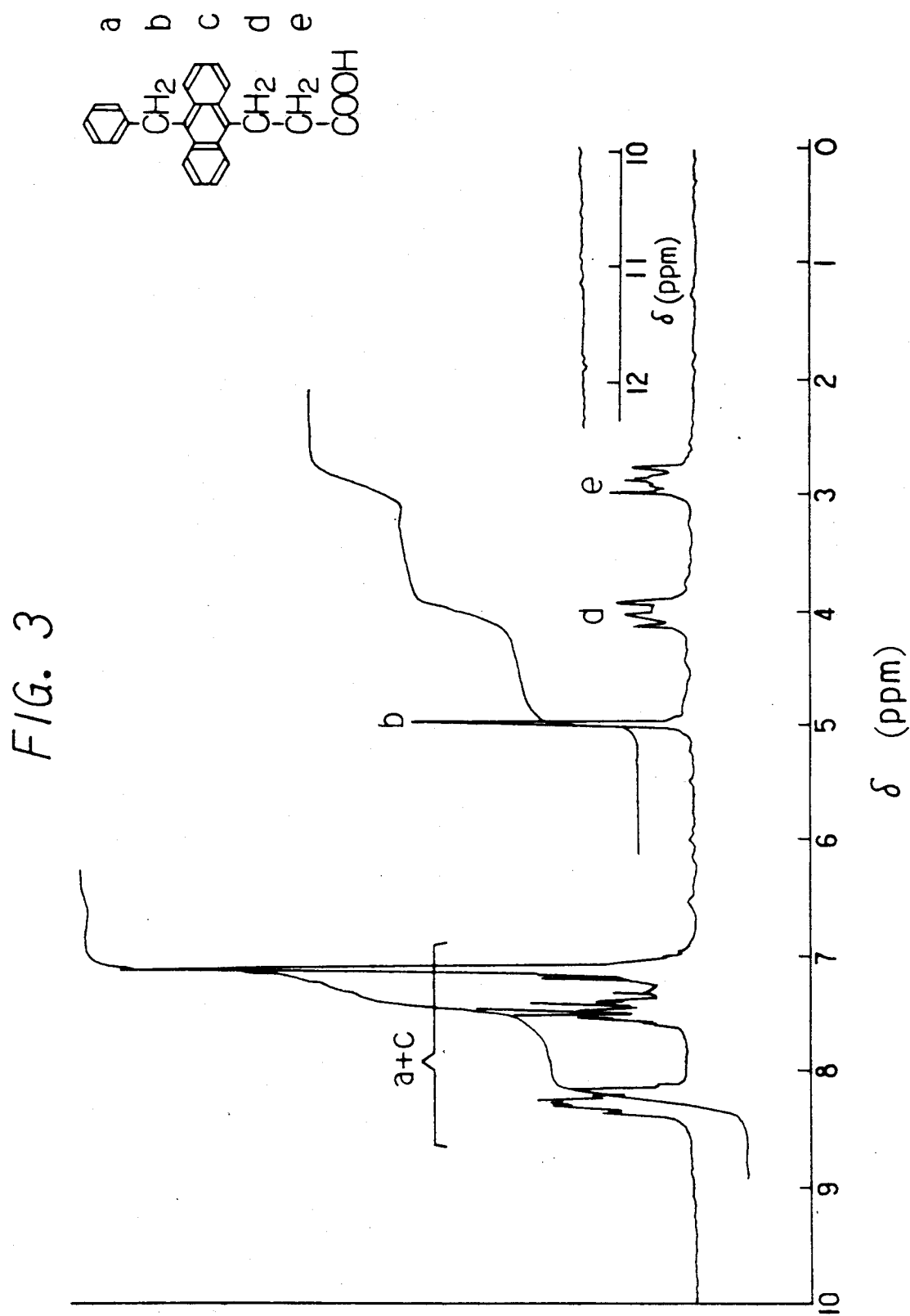

Elementary Analysis:
Calculated (%): H 5.88 C 84.71 O 9.41
Found (%): H 5.88 C 84.82 O 9.30
IR Spectrum Analysis (KBr): Described in FIG. 2
$^1$H-NMR Spectrum Analysis: Described in FIG. 3

In the elementary analysis, oxygen was measured by using an oxygen corder available from Kabushiki Kaisha Yanagimoto Seisakusho. The $^1$H-NMR spectrum was measured in CDCl$_3$ at room temperature with 80 MHz.

EXAMPLE 2

9-Phenylethyl-10-chloromethylanthracene was synthesized from 2-bromoethylbenzene through 9-phenylethylanthracene in the same manner as in Example 1.

Figure 4:
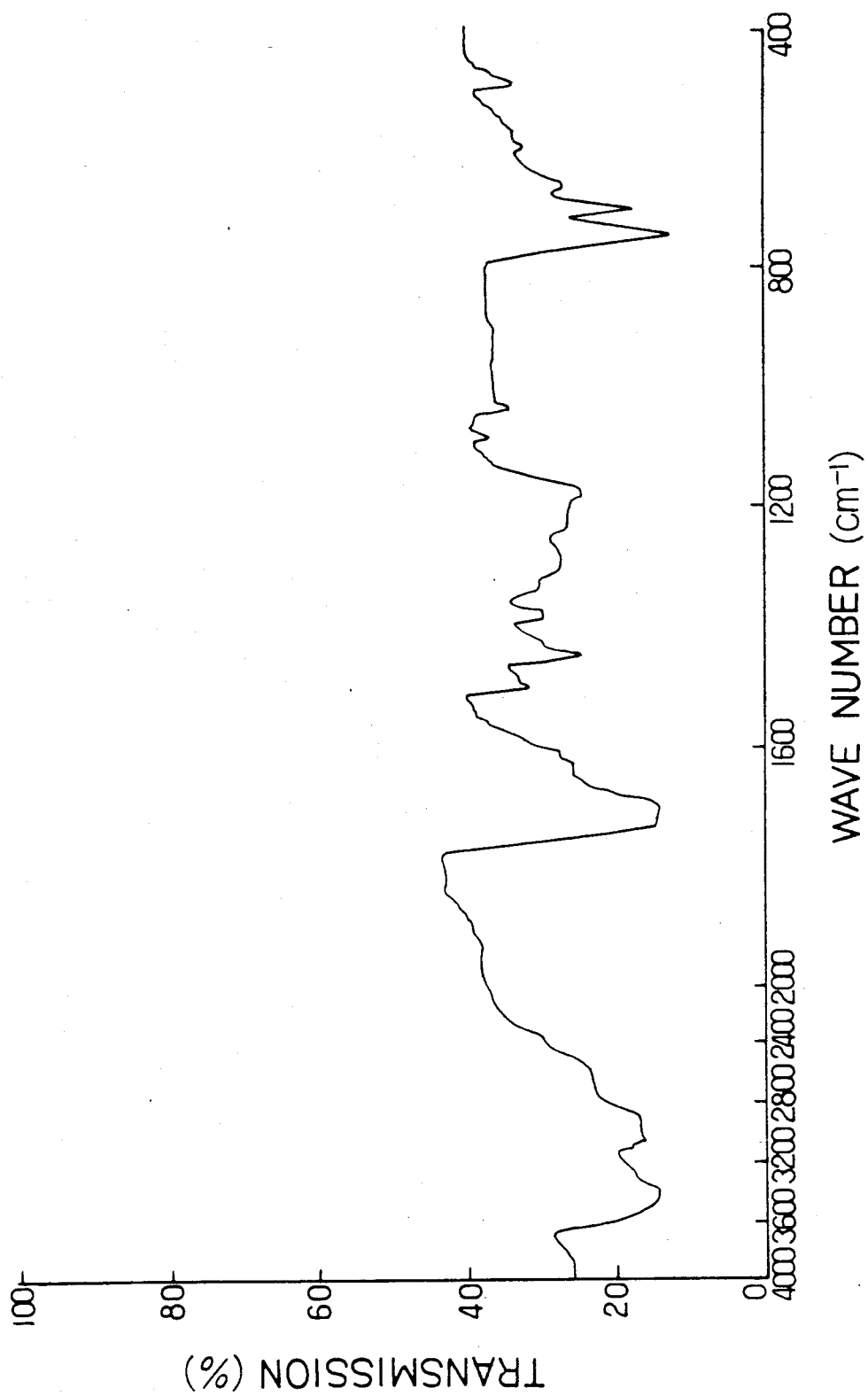
FIG. 4 is an IR spectrum chart of the free hydrolyzed product synthesized in Example 2.

The same procedures in Example 1 were repeated by using 1.2 g of 9-phenylethyl-10-chloromethylanthracene and diethyl sodiomalonate [NaCH(COOC$_2$H$_5$)$_2$] to give a crude malonate reaction product, and the malonate product was hydrolyzed to give 0.7 g of a free hydrolyzed product (mp: 173° to 175° C.). The IR spectrum chart is shown in FIG. 4.

The free hydrolyzed product was thermally decomposed and recrystallized in the same manner as in Example 1 to obtain 0.2 g of a yellow crystal (mp: 187° to 188° C.). The crystal was identified as β-(9-phenylethyl-10-anthryl)propionic acid by means of the following analyses.

Figure 5:
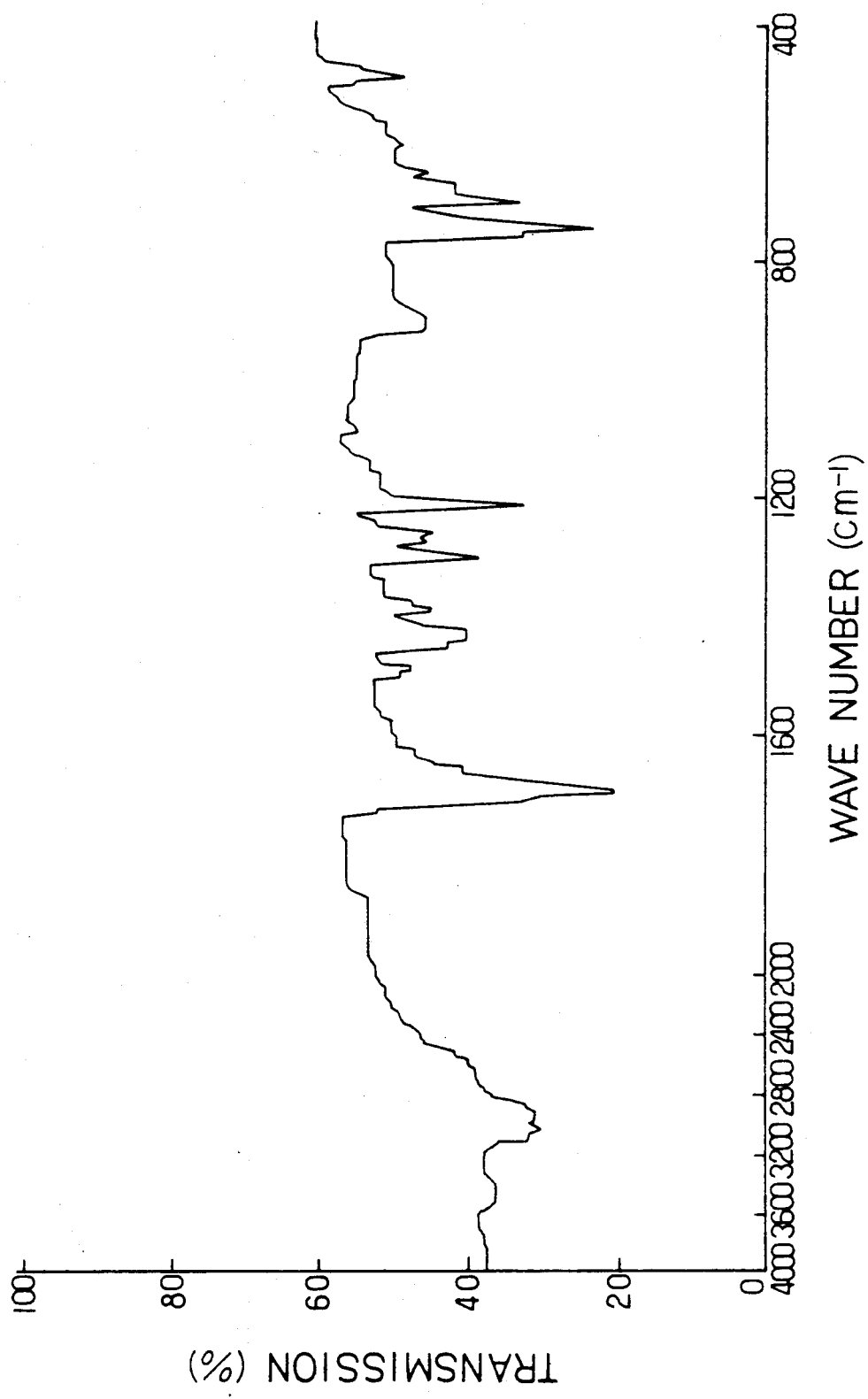
FIGS. 5 and 6 are an IR spectrum chart and an NMR spectrum chart of β(9-phenylethyl-10-anthryl)-propionic acid synthesized in Example 2, respectively.
Figure 6:
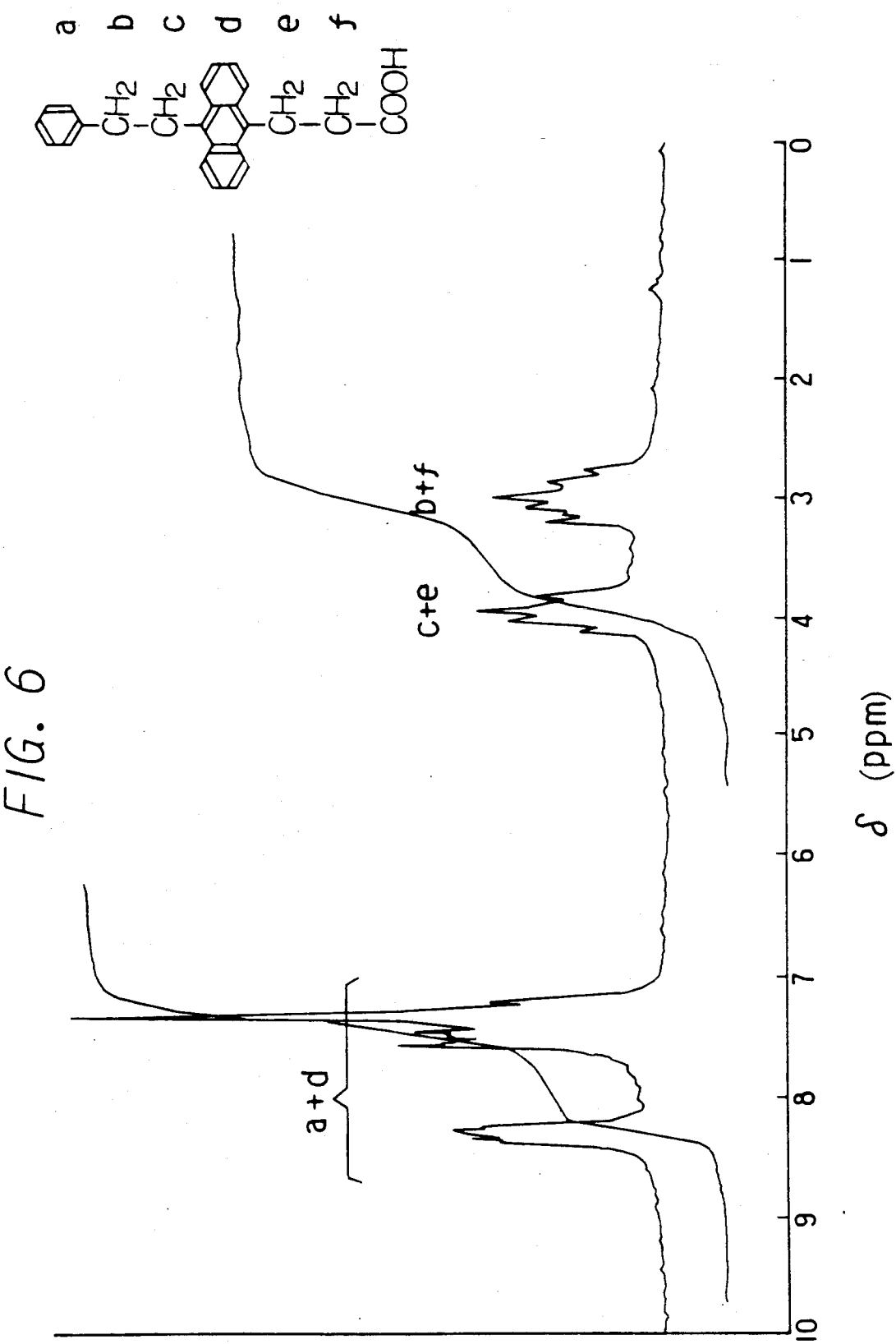

Elementary Analysis:
Calculated (%): H 6.21 C 84.75 O 9.04
Found (%): H 6.32 C 85.01 O 9.07
IR Spectrum Analysis (KBr): Described in FIG. 5
$^1$H-NMR Spectrum Analysis (CDCl$_3$; room temp.; 80 MHz): Described in FIG. 6

By using the β-(9-phenylethyl-10-anthryl)-propionic acid, a Langmuir-Blodgett film consisting of 69 layers was prepared on an aluminum electrode, and Au electrode was formed on the film. When applying a direct voltage of 20V/cm, the film radiated a blue light having a brightness of 0.1 fL.

When using a Langmuir-Blodgett film of 69 layers of β-(9-n-butyl-10-anthryl)propionic acid (mp: 152° C.) instead of β-(9-phenethyl-10-anthryl)propionic acid, the radiated blue light had a brightness of only 0.01 fL.

What we claim is:

1. An electroluminescent device containing a Langmuir-Blodgett film prepared from an amphiphilic compound having the formula (V):

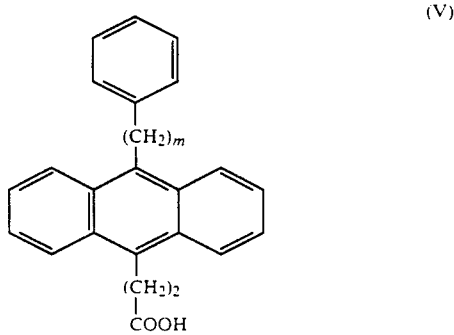

wherein m is 1 or 2.

2. An electroluminescent device according to claim 1, wherein m is 2.

* * * * *